United States Patent
Rusek et al.

(10) Patent No.: US 8,344,193 B2
(45) Date of Patent: Jan. 1, 2013

(54) BIOGENIC TURBINE AND DIESEL FUEL

(75) Inventors: John J. Rusek, West Lafayette, IN (US); Jonathon D. Ziulkowski, West Lafayette, IN (US); Philip J. Catania, West Lafayette, IN (US); Donald L. Bower, West Lafayette, IN (US)

(73) Assignee: Swift Fuels, LLC, West Lafayette, IN (US)

( * ) Notice: Subject to any disclaimer, the term of this patent is extended or adjusted under 35 U.S.C. 154(b) by 311 days.

(21) Appl. No.: 12/788,010

(22) Filed: May 26, 2010

(65) Prior Publication Data

US 2010/0298615 A1    Nov. 25, 2010

Related U.S. Application Data

(63) Continuation-in-part of application No. 12/717,480, filed on Mar. 4, 2010, which is a continuation-in-part of application No. 12/139,428, filed on Jun. 13, 2008, now Pat. No. 8,049,048, which is a continuation-in-part of application No. 11/881,565, filed on Jul. 27, 2007, now abandoned.

(60) Provisional application No. 60/833,589, filed on Jul. 27, 2006.

(51) Int. Cl.
  *C10L 1/06* (2006.01)
  *C10L 1/16* (2006.01)
(52) U.S. Cl. .......................................... 585/1; 585/14
(58) Field of Classification Search .............. 585/1, 14
  See application file for complete search history.

(56) References Cited

U.S. PATENT DOCUMENTS

| | | | | |
|---|---|---|---|---|
| 2,401,983 | A * | 6/1946 | Stanly et al. | 585/14 |
| 2,593,561 | A * | 4/1952 | Herbst et al. | 44/454 |
| 6,353,143 | B1 * | 3/2002 | Fang et al. | 585/1 |
| 7,141,083 | B2 | 11/2006 | Jordan | |
| 2004/0020106 | A1 | 2/2004 | Tack et al. | |
| 2008/0244962 | A1 | 10/2008 | Abhari et al. | |
| 2009/0000185 | A1 | 1/2009 | Aulich et al. | |

FOREIGN PATENT DOCUMENTS

WO    2008013922 A1    1/2008

OTHER PUBLICATIONS

Colket et al., Development of an Experimental Database and Kinetic Models for Surrogate Jet Fuels, Mar. 1, 2007, American Institute of Aeronautics and Astronautics, pp. 1-21.*
International Search Report and Written Opinion issued on Oct. 19, 2011, in corresponding International Application No. PCT/US2011/037505.

* cited by examiner

*Primary Examiner* — Cephia D Toomer
(74) *Attorney, Agent, or Firm* — Woodard, Emhardt, Moriarty, McNett & Henry LLP

(57) ABSTRACT

The present invention provides fully renewable turbine and diesel fuels derived completely from biomass sources. In one embodiment the fully renewable turbine fuel is comprised of mesitylene and at least one alkane. Preferably, the turbine fuel comprises from about 50 to 99 wt % mesitylene and from about 1 to 50 wt % of at least one alkane. In another embodiment the diesel fuel comprises mesitylene, octadecane, and optionally octane or nonane. Preferably, the diesel fuel comprises from about 50 to 99 wt % mesitylene, and from about 1 to 50 wt % octadecane. These biomass derived fuels may be formulated to have a wide range of cetane values and differing freezing and boiling points.

17 Claims, No Drawings

BIOGENIC TURBINE AND DIESEL FUEL

REFERENCE TO RELATED APPLICATIONS

This is a continuation-in-part of U.S. patent application Ser. No. 12/717,480, filed Mar. 4, 2010 which is a continuation-in-part of U.S. patent application Ser. No. 12/139,428, filed Aug. 13, 2008, which is a continuation-in-part of U.S. patent application Ser. No. 11/881,565, filed Jul. 27, 2007, which claims priority of provisional U.S. Patent Application Ser. No. 60/833,589, filed Jul. 27, 2006, the contents of all of which are incorporated herein by reference.

FIELD OF THE INVENTION

The present invention relates in general to an engine fuel produced from renewable materials and, in particular, the present invention provides a non-petroleum based fuel which can be produced fully from renewable materials. In one embodiment, one of the fuels of the present invention may be formulated into a variety of aviation fuels, including fuels employed in aviation turbine engines. In another embodiment, these biogenic fuels can be used in various types of diesel engines.

BACKGROUND OF THE INVENTION

With the end of cheap oil and the mounting peak of world oil production, it is recognized that petroleum is a non-renewable resource and will eventually be depleted. This realization has sparked a renewed interest in the development of renewable sources for fuel. This is particularly true in the case of aviation fuels used in internal combustion engines, such as in turbine engines as well as for jet fuels.

In the United States, the Federal Aviation Administration (FAA) is responsible for setting the technical standards for aviation fuels through the American Society for Testing and Materials (ASTM). Currently, the FAA uses as a standard for aviation fuel the 100LL aviation gasoline. To qualify as a 100 octane aviation fuel, any new fuel must comply with the current aviation gasoline specification ASTM D910. This is true whether the new fuel is based on petroleum or a chemical or chemical combination.

Ethanol-based fuels for internal combustion engines have been available for roughly five decades. The State of California originated mandatory oxygenation of motor fuels, which includes ethanol-based fuels, partly to decrease the wholesale cost of fuel, and to a lesser extent to reduce air pollution per gallon of gasoline consumed. Effectively, since ethanol-based fuels have lower energy, pollution is generally increased per mile. A key benefit of ethanol-based fuels is that they have a slightly higher octane number than ethanol-free gasoline. This is the reason many oil companies provide high ethanol containing premium fuels and lower ethanol regular grades of gasoline. Renewable fuels made from some chemical species other than ethanol have been found to exhibit significantly higher octane numbers and increased energy per unit volume when compared to commercial fuels and ethanol-based fuels.

Octane (Power)

Octane number is a measure of the effectiveness of power production. It is a kinetic parameter, therefore difficult to predict. Oil companies compiled volumes of experimental octane data (for most hydrocarbons) for the Department of Defense in the 1950's. The method used to obtain this dynamic parameter is discussed in the next paragraph. 2,2,4-trimethyl pentane (isooctane) has a defined octane number of 100, and n-heptane has a defined octane number of 0, based on experimental tests. Octane numbers are linearly interpolated and extrapolated by this method; hence predictions for mixes can be made once pure sample values are determined.

Automobile gasoline is placarded at the pump as the average of Research and Motor octane numbers. These correlate to running a laboratory test engine (CFR) under less severe and more severe conditions, respectively. True octane numbers lie between the Research and Motor octane values. Aviation fuel has a "hard" requirement of 100 MON (motor octane number); ethanol has a MON of 96, which makes its use only viable when mixed with other higher octane components. Conventional 100LL (i.e., 100 octane low lead) contains about 3 ml of tetraethyl lead per gallon.

Range (Energy)

The inherent energy contained within gasoline is directly related to mileage, not to octane number. Automobile gasoline has no energy specification, hence no mileage specification. In contrast, aviation fuels, a common example being 100LL (100 octane low lead), have an energy content specification. This translates to aircraft range and to specific fuel consumption. In the octane examples above, i-octane and n-heptane had values of 100 and 0, respectively. From an energy perspective, they contain heat of combustion values of 7.84 and 7.86 kcal/ml, respectively, which is the reverse of what one would expect based on power developed. Aircraft cannot compromise range due to the sensitivity of their missions. For this reason, energy content is equally important as MON values.

The current production volume of 100LL is approximately 850,000 gallons per day. 100LL has been designated by the Environmental Protection Agency (EPA) as the last fuel in the United States to contain tetraethyl lead. This exemption will likely come to an end in the near future (2010).

Although a number of chemical compounds have been found to satisfy the motor octane number for 100LL octane aviation fuel, they fail to meet a number of other technical requirements for aviation fuel. This is true, for example, for isopentane, 90MON, and trimethyl benzene 136MON. For example, pure isopentane fails to qualify as an aviation fuel because it does not pass the ASTM specification D909 for supercharge ON, ASTM specification D2700 for motor octane number, and ASTM specification D5191 for vapor pressure. Pure sym-trimethyl benzene (mesitylene) also fails to qualify as an aviation fuel because it does not pass ASTM specification D2386 for freeze point, ASTM specification D5191 for vapor pressure, and ASTM specification D86 for the 10% distillation point.

The fermentation of a biomass using microbes to produce acetone and butanol was first discovered by Chaim Weizmann in 1916 and is described in U.S. Pat. No. 1,315,585 and other corresponding patents throughout the world. This process known as the Weizmann process was used by both Great Britain and the United States in World Wars I and II to produce acetone for the production of cordite used in making smokeless powder. Unfortunately, this method is energy intensive, and accordingly uneconomical.

A number of methods are known for making mesitylene from acetone and include, for example:
(1) Liquid phase condensation in the presence of strong acids, e.g. sulfuric acid and phosphoric acid as described in U.S. Pat. No. 3,267,165 (1966);
(2) Vapor phase condensation with tantalum containing catalysts as described in U.S. Pat. No. 2,917,561 (1959);
(3) Vapor phase condensation using as catalyst the phosphates of the metals of group IV of the periodic system of elements, e.g. titanium, zirconium, hafnium and tin as described in U.S. Pat. No. 3,94,079 (1976);

(4) Vapor phase reaction in the presence of molecular hydrogen and a catalyst selected from alumina containing chromia and boria as described in U.S. Pat. No. 3,201,485 (1965);

(5) Vapor phase reaction using catalysts containing molybdenum as described in U.S. Pat. No. 3,301,912 (1967) or tungsten as described in U.S. Pat. No. 2,425,096, a vapor phase reaction over a niobium supported catalyst with high selectivity. The catalyst is preferably made by impregnating a silica support with an ethanolic solution of $NCl_5$ or an aqueous solution of Nb in order to deposit 2% Nb by weight and by calcining the final solid at 550° C. for 18 hours. At 300° C., the condensation of acetone produces mainly mesitylene (70% selectivity) at high conversion (60-80% wt) as described in U.S. Pat. No. 5,087,781.

It is also known in the art to dimerize acetone to form isopentane. This process involves first dimerizing acetone to form diacetone alcohol which is then dehydrated to form mesitytl oxide. The mesityl oxide then undergoes gas phase reformation hydrogenation to form isopentane.

It is also known from U.S. Pat. No. 7,141,083 to produce a fuel comprising mesitylene and straight-chain alkanes (i.e., hexanes, heptanes, octanes, nonanes and the like) from plant oil, such as corn oil. The composition of corn oil is shown in Table 1 below. The predominant components of corn oil are stearic, palmitic, oleic, and linoleic acids of the free fatty acids.

It is an object of the present invention to provide biogenic fuels that effectively replace petroleum-based fuels currently used in engines.

It is another object of the present invention to provide fully renewable fuels for other internal combustion/heat engines as well.

It is a further object of the present invention to provide high energy renewable fuels for use in turbines and other heat engines by the same methodology; the energy content and physical properties of the renewable components being tailored to the type of engine to be fueled.

It is another object of the present invention to provide a binary mixture of components which meet the technical specifications for turbine engines.

It is another object of the present invention to provide a non-petroleum based aviation fuel which meets the technical specifications of the Federal Aviation Administration for petroleum-based turbine fuels.

It is still another object of the present invention to provide a process for the production from a biomass of the components of binary chemicals and ternary mixtures which satisfy the technical specifications for both turbine and diesel engines.

SUMMARY OF THE INVENTION

In order to achieve the objects of the present invention, the present inventors have arduously carried out research and endeavored to provide fully renewable fuels, preferably derived from a biomass having a high energy content, such as corn oils. Accordingly, in a first preferred embodiment of the present invention, the present inventors provide a renewable turbine fuel comprised of mesitylene and at least one alkane.

In a second preferred embodiment of the present invention, there is provided in the first preferred embodiment a turbine fuel comprising from about 50 to 99 wt % mesitylene, and from about 1 to 50 wt % of one or more alkanes.

In a third preferred embodiment of the present invention, there is provided in the first preferred embodiment a turbine fuel comprising from about 60 to 90 wt % mesitylene.

In a fourth preferred embodiment of the present invention, there is provided in the third preferred embodiment a turbine fuel comprising from about 10 to 40 wt % tetradecane.

In a fifth preferred embodiment of the present invention, there is provided in the first preferred embodiment a turbine fuel comprising from about 75 to 85 wt % mesitylene, and from about 15 to 25 wt % tetradecane.

In a sixth preferred embodiment of the present invention, there is provided in the first preferred embodiment a turbine fuel comprising from about 80 wt % mesitylene, and about 20 wt % tetradecane.

In a seventh preferred embodiment of the present invention, there is provided a turbine fuel comprising mesitylene, tetradecane, and heptane.

In an eighth preferred embodiment of the present invention, there is provided a turbine fuel in the seventh preferred embodiment, in which the fuel comprises from about 15 to 75 wt % heptane, from about 20 to 65 wt % mesitylene, and from about 5 to 20 wt % tetradecane.

In a ninth preferred embodiment of the present invention, there is provided in the seventh preferred embodiment a turbine fuel comprising from about 35 to 55 wt % mesitylene, from about 10 to 20 wt % tetradecane, and from about 20 to 50 wt % heptane.

In a tenth preferred embodiment of the present invention, there is provided in the seventh preferred embodiment a turbine fuel comprising from about 42 to 48 wt % mesitylene, from about 15 to 20 wt % tetradecane, and from about 32 to 43 wt % heptane.

In an eleventh preferred embodiment of the present invention, there is provided in the seventh preferred embodiment a turbine fuel comprising about 45 wt % mesitylene, about 17.5 wt % tetradecane, and about 37.5 wt % heptane.

In a twelfth preferred embodiment of the present invention, there is provided in the seventh preferred embodiment a turbine fuel comprising from about 1 to 25 wt % mesitylene, from about 25 to 60 wt % tetradecane, and from about 15 to 74 wt % heptane.

In a thirteenth preferred embodiment of the present invention, there is provided in the seventh preferred embodiment a turbine fuel comprising from about 5 to 20 wt % mesitylene, from about 30 to 50 wt % tetradecane, and from about 30 to 65 wt % heptane.

In a fourteenth preferred embodiment of the present invention, there is provided in the seventh preferred embodiment a turbine fuel comprising about 10 wt % mesitylene, about 40 wt % tetradecane, and about 50 wt % heptane.

In a fifteenth preferred embodiment of the present invention, there is provided a diesel fuel comprising mesitylene, octadecane and, optionally, or nonane.

In a sixteenth preferred embodiment of the present invention, there is provided in the fifteenth preferred embodiment a diesel fuel comprising from about 50 to 99 wt % mesitylene, and from about 1 to 50 wt % octadecane.

In a seventeenth preferred embodiment of the present invention, there is provided in the fifteenth preferred embodiment a diesel fuel comprising from about 60 to 90 wt % mesitylene, and from about 10 to 40 wt % octadecane.

In an eighteenth preferred embodiment of the present invention, there is provided in the fifteenth preferred embodiment a diesel fuel comprising from about 65 to 75 wt % mesitylene, and from about 25 to 35 wt % octadecane.

In a nineteenth preferred embodiment of the present invention, there is provided in the fifteenth preferred embodiment a diesel fuel comprising about 70 wt % mesitylene and about 30 wt % octadecane.

In a twentieth preferred embodiment of the present invention, there is provided in the fifteenth preferred embodiment a diesel fuel comprising from about 20 to 65 wt % mesitylene, from about 30 to 60 wt % octane, and from about 5 to 20 wt % octadecane.

In a twenty-first preferred embodiment of the present invention, there is provided in the fifteenth preferred embodiment a diesel fuel comprising from about 25 to 45 wt % mesitylene, from about 40 to 60 wt % octane, and from about 20 to 50 wt % octadecane.

In a twenty-second preferred embodiment of the present invention, there is provided in the fifteenth preferred embodiment a diesel fuel comprising from about 32 to 35 wt % mesitylene, from about 45 to 58 wt % octane, and from about 10 to 20 wt % octadecane.

In a twenty-third preferred embodiment of the present invention, there is provided in the fifteenth preferred embodiment a diesel fuel comprising about 35 wt % mesitylene, about 50 wt % octane, and about 15 wt % octadecane.

Other preferred embodiments use the systems (mesitylene-dodecane-hexane; mesitylene-hexadecane-octane—in general (mesitylene-C2n alkane-Cn alkane) as well as (mesitylene-C2n alkane)—from n=6 through n=12

DETAILED DESCRIPTION OF THE INVENTION

As discussed above, the present invention provides a non-petroleum-based renewable fuel comprised of fully renewable components, i.e., components derived from biosources such as corn. This fuel has several variants, the preferred variants being turbine fuel and diesel fuel. Advantageously, the components of the fuels discussed above are all derivable from plant or animal oils, and the product can be tailored to the input stock. In general, plant oils are preferred due to their lower molecular weight products.

Both the turbine fuels and the diesel fuels of the present invention provide an overall mix and match with discreet components derivable from all plant or animal oils, and the product can be tailored to the input stock. In general, plant oils are preferred as the base stock for production of the fuel component of the composition, due to their lower molecular weight products. With regards to same, the fuel component can be derived from various plant source bio-oils. For example, the bio-oil may include soybean oil, rapeseed oil, canola oil or corn oil, palm oil, and combinations thereof. Most preferably, corn oil is utilized as the bio-oil component because of its enhancement of energy, fuel's physical properties, and lubricity properties. Corn oil is derived directly from the corn germ. The components of corn oil are shown below in Table 1.

TABLE 1

| FFA | C Number | Unsaturation | As is |
|---|---|---|---|
| Lauric | 12 | 0 | 0% |
| Myristic | 14 | 0 | 0.06% |
| Palmitic | 16 | 0 | 13.81% |
| Palmitoleic | 16 | 1 | 0.19% |
| Margaric | 17 | 0 | 0.07% |
| Stearic | 18 | 0 | 2.19% |
| Oleic | 18 | 1 | 27.86% |
| Linoleic | 18 | 2 | 52.41% |
| a-Linoleic | 18 | 3 | 1.29% |

TABLE 1-continued

| FFA | C Number | Unsaturation | As is |
|---|---|---|---|
| Arachidic | 20 | 0 | 0.45% |
| Eicosenoic | 20 | 1 | 0.35% |
| Eicosadienoic | 20 | 2 | 0.04% |
| Behinic | 22 | 0 | 0.19% |
| Erucic | 22 | 1 | 0.00% |
| Ligoceric | 24 | 0 | 0.24% |
| Others | | | 1.00% |

With reference to Table 1, it can be seen that corn oil contains derivable straight-chain alkanes, namely, n-octadecane and n-hexadecane. Also, it is known that these two alkanes can be cracked to form n-nonane and n-octane, respectively. Also, triacylglycerides are comprised of these fatty acids, compositions shown in Table 1 above. Part of the JetE (and others) thermolysis process is the generation of propane from the triacylglycerides as well.

It is also known that propane can be dehydrogenated to form propyne and hydrogen (which the thermolysis process needs). Propyne can be directly trimerized to mesitylene via the same catalysts used for trimerizing and dehydrating acetone to form mesitylene. It can be seen that bio-oils can be used to produce mesitylene, n-octadecane, n-hexadecane, n-nonane, and n-octane.

With regards to the aromatic hydrocarbon component of these fuels, unlike conventional petroleum-based fuels, the present invention comprises aromatic hydrocarbons derived from acetone, a fully renewable source. Most preferably, the aromatic hydrocarbon is mesitylene. Mesitylene can conveniently be prepared by the trimerization of acetone or propyne; acetone can be readily prepared from biomass, and propyne can be extracted from natural gas. Mesitylene is preferred, since the acetone or propyne reaction "stops" at the trimer, which makes the conversion high due to lack of significant side-reactions. Mesitylene can be used as an octane and energy enhancing ingredient.

With regards to the straight chain alkanes, the alkanes are preferably derived from biomass, specifically polysaccharides derived from biomass. Straight chain alkanes have the lowest octane number of a given set of alkane isomers; the more branched the molecule, the smoother combusting (higher octane) the molecule exhibits when tested. Preferred straight chain alkanes are utilized in the fuels of the present invention including tetradecane, heptane, octadecane, octane, and nonane. These straight chain alkanes act as octane depressants within the fuel.

Lower straight chain alkanes such as n-pentane, n-butane, propane, and below, have too low of a boiling point to be useful as a main component of the fuels of the present invention. Higher straight chain alkanes, such as n-nonane, n-decane and above, have a high carbon-to-hydrogen molecule fraction (>0.444). Straight chain alkanes can be used to suppress the octane of a given fuel, while maintaining a high energy content per unit volume. Higher alkanes can be used in diesel and jet turbine applications.

Turbine Fuels:

In particular, when the fuel is tailored to turbine engine application, as provided in the first preferred embodiment herein, a first renewable turbine fuel comprising two components is provided, namely from 50-99 wt % mesitylene and from 1-50 wt % of one more alkanes, more preferably 75-85 wt % of mesitylene and 10-40 wt % of tetradecane, even more preferably 75-85 wt % of mesitylene and 15-25 wt % of tetradecane, most preferably 80 wt % of mesitylene and 20 wt % of tetradecane.

For turbine applications, if the mesitylene is present in an amount of less than 45 wt %, the freezing point will fall out of specification. Further, if the amount of alkanes, such as tetradecane, is less than 1 wt %, the fuel will be too dense and will not possess a high enough specific energy (net heat of combustion per mass). However, if the amount of alkanes in the turbine fuel composition exceeds 50 wt %, the freezing point will fall out of specification.

In a further embodiment of the present invention, a second renewable turbine fuel comprising three components is provided, namely, from about 1 to 65 wt % of mesitylene, from about 5 to 60 wt % of n-tetradecane or, preferably 5-60 wt % of n-hexadecane, and from about 15 to 75 wt % of heptane. In a preferred embodiment, the second renewable turbine fuel comprises 5 to 55 wt % of mesitylene, from about 5 to 55 wt % of n-tetradecane or, preferably 5-55 wt % of n-hexadecane, and from about 20 to 65 wt % of heptane. In a more preferred embodiment, the second renewable turbine fuel comprises 5 to 48 wt % of mesitylene, from about 15 to 45 wt % of n-tetradecane or, preferably 15-45 wt % of n-hexadecane, and from about 32 to 60 wt % of heptane. In a highly preferred embodiment, the second renewable turbine fuel comprises 45 wt % of mesitylene, 17.5 wt % of n-tetradecane or, preferably 17.5 wt % of n-hexadecane, and 50 wt % of heptane. In another highly preferred embodiment, the second renewable turbine fuel comprises 10 wt % of mesitylene, 40 wt % of n-tetradecane or, preferably 50 wt % of n-hexadecane, and 50 wt % of heptane.

In this turbine fuel application, if the mesitylene is present in an amount of less than 1 wt %, then the fuel will fall below the specified density range, will not provide the necessary specific energy per gallon, and may not meet the freezing point specification, whereas if the mesitylene is present in an amount greater than 65 wt %, then the density will be outside the high end of the specified range and the net heat of combustion by mass will fall below the specified limit. Further, if the amount of alkane, such as tetradecane, is less than 5 wt %, the fuel composition will possess a net heat of combustion by mass that is too low, whereas if the alkane is present in an amount greater than 50 wt %, then the freezing point of the fuel will be too high and the density will fall below the specified range.

In addition, the heptane component, which is preferably n-heptane, provides a large decrease in freezing point and a high net heat of combustion by mass. If heptane is present in an amount of less than 15 wt %, then the fuel may possess too high a freezing point, whereas if the amount of heptanes exceeds 74 wt %, then the density will be too low and the specific energy per gallon will be significantly decreased, resulting in fewer 'miles per gallon' out of the fuel.

In the above two turbine fuel formulations, mesitylene is added for the high energy per gallon, and to maintain the density (up) to within required ASTM specifications. One of the preferred ternary turbine formulations comprises about 10 wt % mesitylene, about 40 wt % n-tetradecane, and about 50 wt % n-heptane. In this formulation, it was found that this weight percent of mesitylene kept the density from getting too low; n-tetradecane was found to provide the formulation with a high energy per pound; and n-heptane was found to keep the freezing point of the composition down to within specifications (as well as provide a very high energy per pound). Further, as mentioned above, in a preferred embodiment, n-hexadecane can be used in place of n-tetradecane, and n-octane can be used in place of n-heptane, in this biogenic fuel.

To test the characteristics of the turbine fuels of the present invention, the present inventor prepared three test compositions, denoted below in Table 1 as Turbine Test Fuel A, B and C, respectively. Then, the physical properties of each test fuel composition were determined using standard accepted methods, namely the test methods used in ASTM D 1655, which is the specification for Jet A and Jet A-1 Aviation Turbine Fuels.

TABLE 2

|  | Turbine Test Fuel A | Turbine Test Fuel B | Turbine Test Fuel C |
| --- | --- | --- | --- |
| Mesitylene (wt %) | 80.0 | 45.0 | 10.0 |
| Heptane (wt %) | 0.0 | 37.5 | 50.0 |
| Tetradecane (wt %) | 20.0 | 17.5 | 40.0 |
| Boiling Point (° K) | 454.8 | 427.8 | 438.7 |
| Freezing Point (° K) | 235.6 | 218.4 | 225.3 |
| Cetane Number (CN) | 31.2 | 44.6 | 67.9 |
| Net Heat Of Combustion (MJ/kg) | 41.61 | 42.87 | 43.99 |
| Net Heat Of Combustion (MJ/L) | 35.15 | 33.41 | 32.27 |
| Density (g/cc) | 0.8447 | 0.7793 | 0.7335 |

As illustrated above, the test turbine fuels of the present invention have net heats of combustion that vary greatly. Turbine Test Fuel B is what most closely matches current Jet A, based on the ASTM D 1655 specification. All properties fall within the parameters of that specification. Turbine Test Fuel A should provide 5% greater energy per gallon compared to 'average' Jet A because of the higher net heat of combustion by volume. This results in extended range of the aircraft using this fuel. The freezing point of this fuel is outside of, but within 3 degrees Celsius of, the maximum freezing point limit of D 1655, and the density is within 0.005 g/cc of the maximum density limit.

This causes the fuel to not meet the specification, but an additive may be included before reaching the end user to correct those small deficiencies. Turbine Test Fuel C has a high net heat of combustion by mass and a low density. This means that the fuel will be significantly lighter than current turbine fuel; weight savings are always important in aviation. The lower net heat of combustion by volume, however, results in less range per gallon.

Diesel Fuels

In a further embodiment of the present invention, a renewable (biogenic) diesel fuel is provided which, like the above first and second renewable turbine fuels, may be comprised of two or three components, namely mesitylene and two alkanes. However, specifically, in the case of diesel fuels with high energy per gallon, n-octadecane is preferably used in place of n-tetradecane because of the higher density and increased net heat of combustion by volume. Further, n-octane or n-nonane is used in place of n-heptane in the diesel application for the same reasons. Like the above turbine fuels, mesitylene is provided in the diesel fuel to provide high energy per pound.

To confirm the characteristics of the diesel fuel composition of the present invention, two diesel test fuels, denoted as Diesel Test Fuel A and B, respectively, were prepared. The physical characteristics of same were then tested using standard accepted methods, which are listed in ASTM D 975, the specification for all diesel fuel oils. The results of these tests are shown below in Table 3 below.

TABLE 3

|  | Diesel Test Fuel A | Diesel Test Fuel B |
| --- | --- | --- |
| Mesitylene (wt %) | 70 | 35 |
| Octane (wt %) | 0 | 50 |
| Octadecane (wt %) | 30 | 15 |
| Boiling Point (° K) | 483.3 | 441.0 |
| Freezing Point (° K) | 247.7 | 232.0 |
| Cetane Number (CN) | 43.5 | 53.8 |
| Net Heat Of Combusion (MJ/kg) | 41.88 | 43.15 |
| Net Heat Of Combustion (MJ/L) | 34.77 | 33.23 |
| Density (g/cc) | 0.8303 | 0.7701 |

As illustrated above, the test turbine fuels of the present invention vary greatly in composition and energy content like the turbine fuels after which they are modeled. Diesel Test Fuel A has a much higher net heat of combustion by volume, leading to an increased range per gallon when operated in a compression-ignition engine. Diesel Test Fuel B has a lower freezing point, allowing for this fuel to be used in colder climates without fear of freezing in the fuel tank.

It was unexpectedly discovered by the present inventors that, by combining the components in the weight ranges called for herein in the fifteenth and twenty-third preferred embodiments herein, a completely non-petroleum-based diesel fuel, fully derivable from renewable biomass sources, could be obtained. Further, it was discovered that the diesel fuel components could be conveniently adjusted to produce an appropriate air to fuel ratio for application in a heat engine. Further, it was unexpectedly discovered that this renewable diesel fuel can be formulated to have very desirable properties by varying the alkane ingredients, with the energy increasing components such as mesitylene.

Alternatively, as called for in the present invention, the present inventors unexpectedly discovered that the renewable diesel fuel of the present invention can be formulated to have a much lower freezing point, as low as 232° K. This is achieved by adding octane or nonane, both which have an extremely low freezing point, up to 60 wt %. Additions above that level may decrease the net heat of combustion by volume, and therefore the miles per gallon achievable, too much to be practical. Accordingly, the renewable diesel fuel of the present invention can be utilized in very cold climates. In addition, the diesel fuel composition of the present invention, preferably containing octadecane and/or octane, possesses sufficiently high energy and cetane number needed for satisfactory diesel fuel applications.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. A biogenic turbine fuel comprising from about 75 to 85 wt % mesitylene, and from about 15 to 25 wt % tetradecane.

2. The biogenic turbine fuel of claim 1, wherein the fuel comprises about 80 wt % mesitylene, and about 20 wt % tetradecane.

3. A turbine fuel comprising from about 15 to 75 wt % heptane, from about 20 to 65 wt % mesitylene, and from about 5 to 20 wt % tetradecane.

4. The turbine fuel of claim 3, wherein the fuel comprises from about 35 to 55 wt % mesitylene, from about 10 to 20 wt % tetradecane, and from about 20 to 50 wt % heptane.

5. The turbine fuel of claim 3, wherein the fuel comprises from about 42 to 48 wt % mesitylene, from about 15 to 20 wt % tetradecane, and from about 32 to 43 wt % heptane.

6. The turbine fuel of claim 3, wherein the fuel comprises about 45 wt % mesitylene, about 17.5 wt % tetradecane, and about 37.5 wt % heptane.

7. A turbine fuel comprising from about 1 to 25 wt % mesitylene, from about 25 to 60 wt % tetradecane, and from about 15 to 74 wt % heptane.

8. The turbine fuel of claim 7, wherein the fuel comprises from about 5 to 20 wt % mesitylene, from about 30 to 50 wt % tetradecane, and from about 30 to 65 wt % heptane.

9. The turbine fuel of claim 7, wherein the fuel comprises about 10 wt % mesitylene, 40 wt % tetradecane, and 50 wt % heptane.

10. A biogenic diesel fuel comprising from about 50 to 99 wt % mesitylene, and from about 1 to 50 wt % octadecane.

11. The biogenic diesel fuel of claim 10, wherein the fuel comprises from about 60 to 90 wt % mesitylene, and from about 10 to 40 wt % octadecane.

12. The biogenic diesel fuel of claim 10, wherein the fuel comprises from about 65 to 75 wt % mesitylene, and from about 25 to 35 wt % octadecane.

13. The biogenic diesel fuel of claim 10, wherein the fuel comprises about 70 wt % mesitylene, and about 30 wt % octadecane.

14. A biogenic diesel fuel comprising from about 20 to 65 wt % mesitylene, from about 30 to 60 wt % octane, and from about 5 to 20 wt % octadecane.

15. The biogenic diesel fuel of claim 14, wherein the fuel comprises from about 25 to 45 wt % mesitylene, from about 40 to 60 wt % octane, and from about 5 to 20 wt % octadecane.

16. The biogenic diesel fuel of claim 14, wherein the fuel comprises from about 32 to 35 wt % mesitylene, from about 45 to 58 wt % octane, and from about 10 to 20 wt % octadecane.

17. The biogenic diesel fuel of claim 16, wherein the fuel comprises about 35 wt % mesitylene, 50 wt % octane, and 15 wt % octadecane.

* * * * *